United States Patent [19]
Kochte

[11] Patent Number: 5,439,654
[45] Date of Patent: Aug. 8, 1995

[54] CUTTER FOR OPENING STERILANT REAGENT CUPS

[75] Inventor: Werner W. Kochte, Kent, Ohio

[73] Assignee: Steris Corporation, Mentor, Ohio

[21] Appl. No.: 264,736

[22] Filed: Jun. 23, 1994

Related U.S. Application Data

[63] Continuation-in-part of Ser. No. 209,412, Mar. 10, 1994.

[51] Int. Cl.$^6$ .............................................. A61L 2/00
[52] U.S. Cl. .................................. 422/292; 141/330; 222/81; 239/271; 422/300; 422/310
[58] Field of Search ............... 422/28, 292, 300, 310; 83/857, 856, 946, 127; 435/295, 30, 31; 222/81; 239/271, 548, 567; 141/329, 330

[56] References Cited

U.S. PATENT DOCUMENTS

| | | | |
|---|---|---|---|
| 2,411,231 | 11/1946 | Rundle et al. | 239/271 |
| 2,645,262 | 7/1953 | Marasco | 146/3 |
| 5,037,623 | 8/1991 | Schneider et al. | 422/292 |
| 5,050,340 | 9/1991 | Seifert | 239/271 X |
| 5,209,909 | 5/1993 | Siegel et al. | 422/292 |

Primary Examiner—Robert J. Warden
Assistant Examiner—Krisanne M. Thornton
Attorney, Agent, or Firm—Fay, Sharpe, Beall, Fagan, Minnich & McKee

[57] ABSTRACT

A door (B) of a countertop decontamination unit (A) is opened to gain access to a well (20) for receiving an anti-microbial agent carrying cup (D). A knife blade assembly (E) includes a central shaft (30) which supports a blade (40). The blade has cutting edges (46) extending in a sloped manner downward from an apex portion (42) of the blade. The blade is divided into two blade sections (44) by the shaft. The cutting edges have beveled peripheral edges which face the front of each blade section. The blades has a curvilinear configuration that defines oppositely facing upper and lower cam surfaces (50, 52). The central shaft has apertures (34a, 34b, 34c) communicating between a shaft interior passage 32 and the outside of the shaft for providing jets of fluid to the inside of the reagent cup for dissolving and flushing the reagent material from the cup. The curved configuration of the blades deflect fluid flow from the apertures into the reagent cup.

18 Claims, 4 Drawing Sheets

CUTTER FOR OPENING STERILANT REAGENT CUPS

This application is a continuation-in-part of application Ser. No. 08/209,412 filed Mar. 10, 1994.

BACKGROUND OF THE INVENTION

The present invention relates to the decontamination art. It finds particular application in conjunction with sterilizing or disinfecting medical, dentistry, veterinary, mortuary, and laboratory instruments and equipment and will be described with particular reference thereto. It will be appreciated, however, that the invention is also applicable to a wide variety of technologies in which reagents are mechanically released at the time of use.

Decontamination connotes the removal of hazardous or unwanted materials, such as bacteria, mold spores, other pathogenic life forms, radioactive dust, and the like. Disinfection connotes the absence of pathogenic or harmful life forms. Sterilization connotes the absence of all life forms, whether pathogenic or not. Often, sterilization is measured against the elimination of bacterial endospores which are the living organisms most resistant to conventional sterilants. Microbial decontamination is used herein as the term generic to both sterilization and disinfection.

Heretofore, medical, dental, surgical, veterinary, and laboratory equipment and instruments have often been sterilized in a steam autoclave. Autoclaves kill life forms with a combination of high temperature and pressure. However, steam autoclaves have several drawbacks. The high temperature and pressure vessels tend to be bulky and heavy. The high temperature and pressure tends to curtail the useful life of the endoscopes, rubber and plastic devices, lenses, bearings, and portions of devices made of polymeric materials, and the like. Moreover, the autoclave sterilizing and cool down cycle is sufficiently long that multiple sets of the medical instruments are commonly required.

Instruments which cannot withstand the pressure or temperature of the oven autoclave are often sterilized with ethylene oxide gas, particularly at larger medical facilities or hospitals. However, the ethylene oxide sterilization technique also has several drawbacks. First, the ethylene oxide sterilization cycle is even longer than the steam autoclave cycle. Another drawback is that ethylene oxide sterilization is sufficiently sophisticated that trained technicians are commonly required, making it unsuitable for physician and dental offices and for other smaller medical facilities. Yet another drawback is that some medical equipment can not be sterilized with ethylene oxide gas.

Liquid sterilization systems have also been utilized for equipment which could not withstand the high temperatures of steam sterilization. Commonly, a technician mixes a liquid sterilant composition and manually immerses the items to be sterilized. The high degree of manual labor introduces numerous uncontrolled and unreported variables into the sterilization process. There are quality assurance problems with the weakening of the sterilants due to aging on the shelf, technician error in the mixing of sterilants, technician error in the control of the immersion times, technician error between immersion and the rinsing of residue, technician error in exposure to the ambient atmosphere after the rinsing step, and the like.

Another problem with the prior art liquid system resides in the corrosive nature of the strong oxidants that are commonly used as liquid sterilants. Normally, the sterilized items are rinsed to remove chemical residues. This rinsing also adds a variable that reduces the assurance the item has been disinfected or sterilized. Once rinsed, the item is susceptible to reinfection by airborne microbes.

In U.S. Pat. No. 5,209,909 also of the assignee herein, a reagent system was described which used only powdered reagents. The powdered reagents were stored in separate compartments in a two-compartment cup. The two-compartment cup was cut open with knife blades and the two reagents were dissolved in high pressure water. The dissolved reagents reacted to form a sterilant solution with buffers, corrosion inhibitors, wetting agent, and the like.

The all powdered formulation has some notable advantages over the liquid peracetic acid system. Severe restrictions by airlines effectively limit the shipment of liquid peracetic acid to surface transportation. Because liquid peracetic acid has a limited shelf life over which full potency can be assured, precise timing is required to ship the liquid peracetic acid sterilant systems overseas and have them arrive with a satisfactory remaining shelf life.

The present invention provides a new and improved cutter assembly which is ideal for opening powdered reagent containers.

SUMMARY OF THE INVENTION

In accordance with one aspect of the present invention, a cutter assembly is provided for cutting open a reagent containing package. The cutting assembly includes a center shaft on which a blade is mounted; the blade has two blade sections on opposite sides of the shaft. The blades have beveled cutting edges to aid in cutting open the reagent package. Fluid for mixing the reagent is provided to the inside of the reagent package through apertures in the shaft.

In accordance with a more limited aspect of the invention the blades of the cutter assembly, on opposite sides of the center shaft, are curvilinear in configuration to define oppositely facing cam surfaces.

In accordance with another aspect of the invention, the central shaft of the cutter assembly has two apertures on the top thereof which provide fluid to the inside of the reagent package.

In a more limited aspect of the invention, the center shaft of the cutter assembly has a pair of apertures on the top thereof, positioned diametrically opposite one another, and another pair of apertures on the lower portion of the shaft, also positioned diametrically opposite one another. Both pairs of apertures are positioned to ensure complete mixing of all reagent material with the mixing fluid, even from the interior corner regions of the reagent package.

In yet another more limited aspect of the invention, the apertures, of which there are a pair on the top of the center shaft and at least two more pairs along the vertical length of the center shaft, are positioned such that fluid released from the apertures is deflected by the blades to aid in the complete mixing of all reagent material.

One advantage of the present invention is that it opens the reagent package such that all dry reagents are completely dissolved.

Another advantage of the present invention is that it facilitates fluid flow into and out of the interior of the reagent package.

Still further advantages of the present invention will become apparent to those of ordinary skill in the art upon reading and understanding the following detailed description of the invention.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
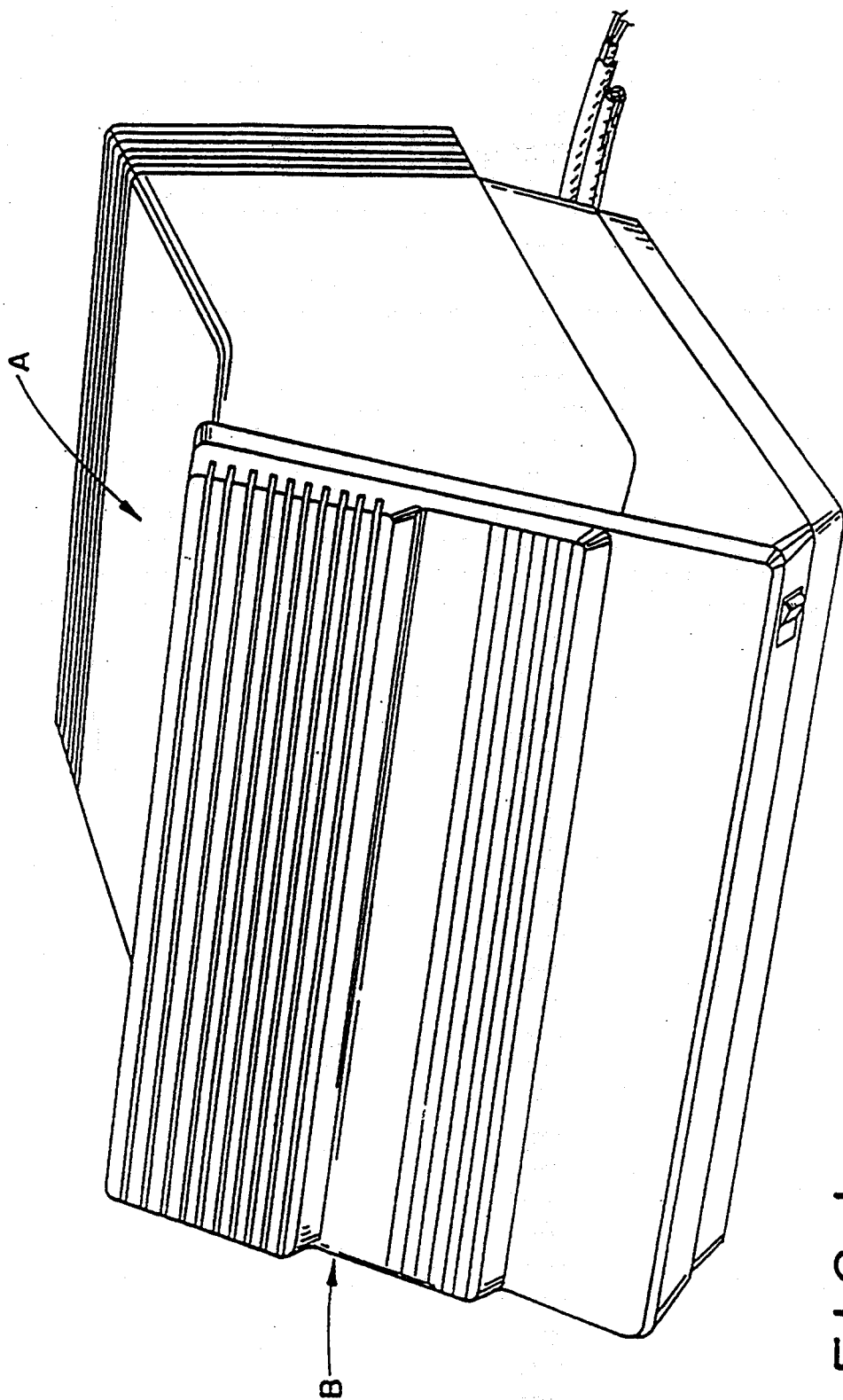
FIG. 1 is a perspective view of a counter top decontamination unit.
Figure 2:
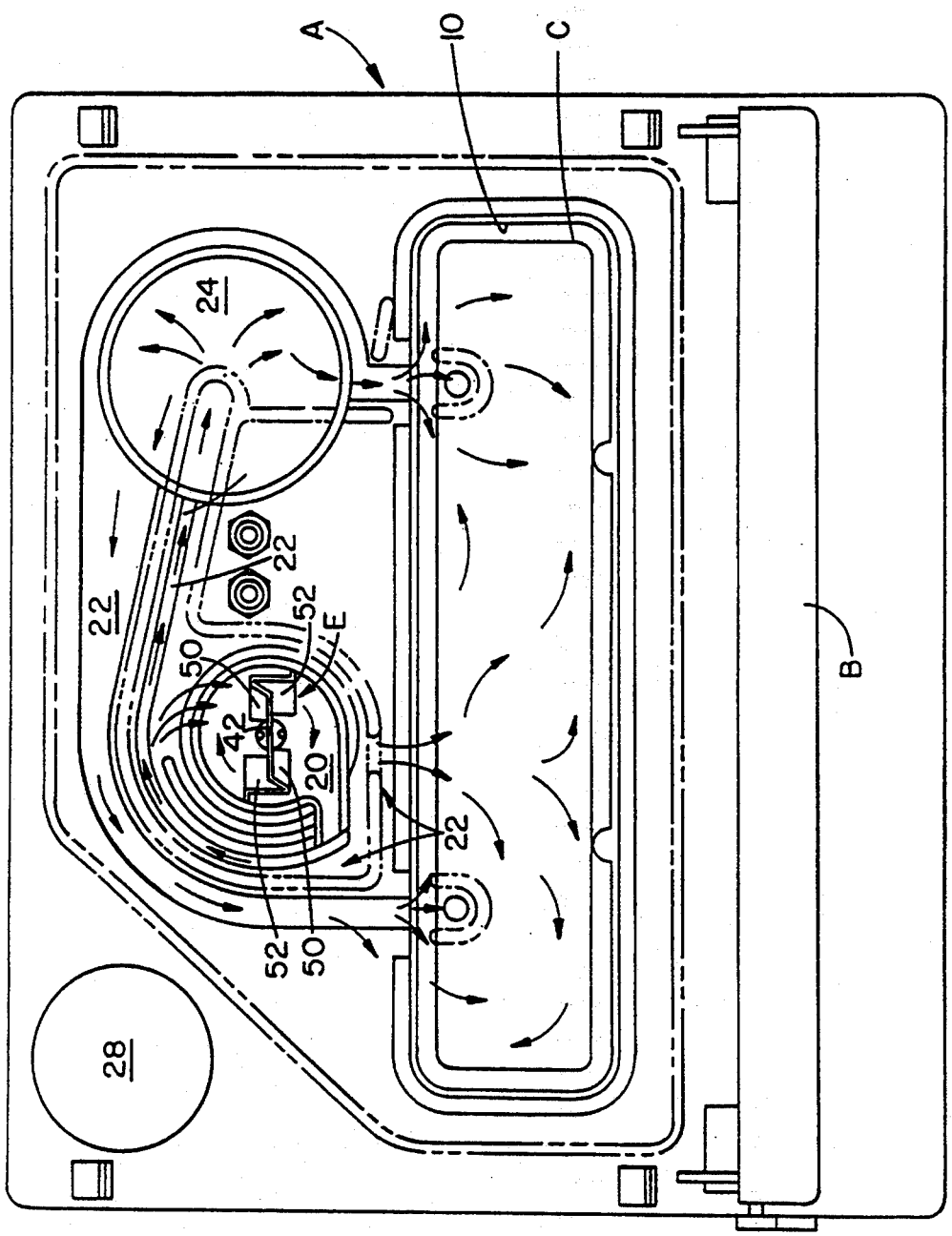
FIG. 2 is a front view of the decontamination unit of FIG. 1 with the front door open.

With reference to FIGS. 1 and 2, a sterilizing apparatus A is configured to sit on a countertop or other convenient work surface. A front door B is manually openable to provide access for inserting a cartridge C and a sterilant cup or ampule D, into the system. Upon insertion of the cup or ampule D, the bottom of the cup or ampule is punctured by an apex of a cutter assembly E. Items to be sterilized are loaded in the cartridge C which is slidably received in a sterilizing or decontamination cartridge receiving chamber 10. The chamber 10 is open at the front to receive a free flow of sterilant through the front.

Figure 3:
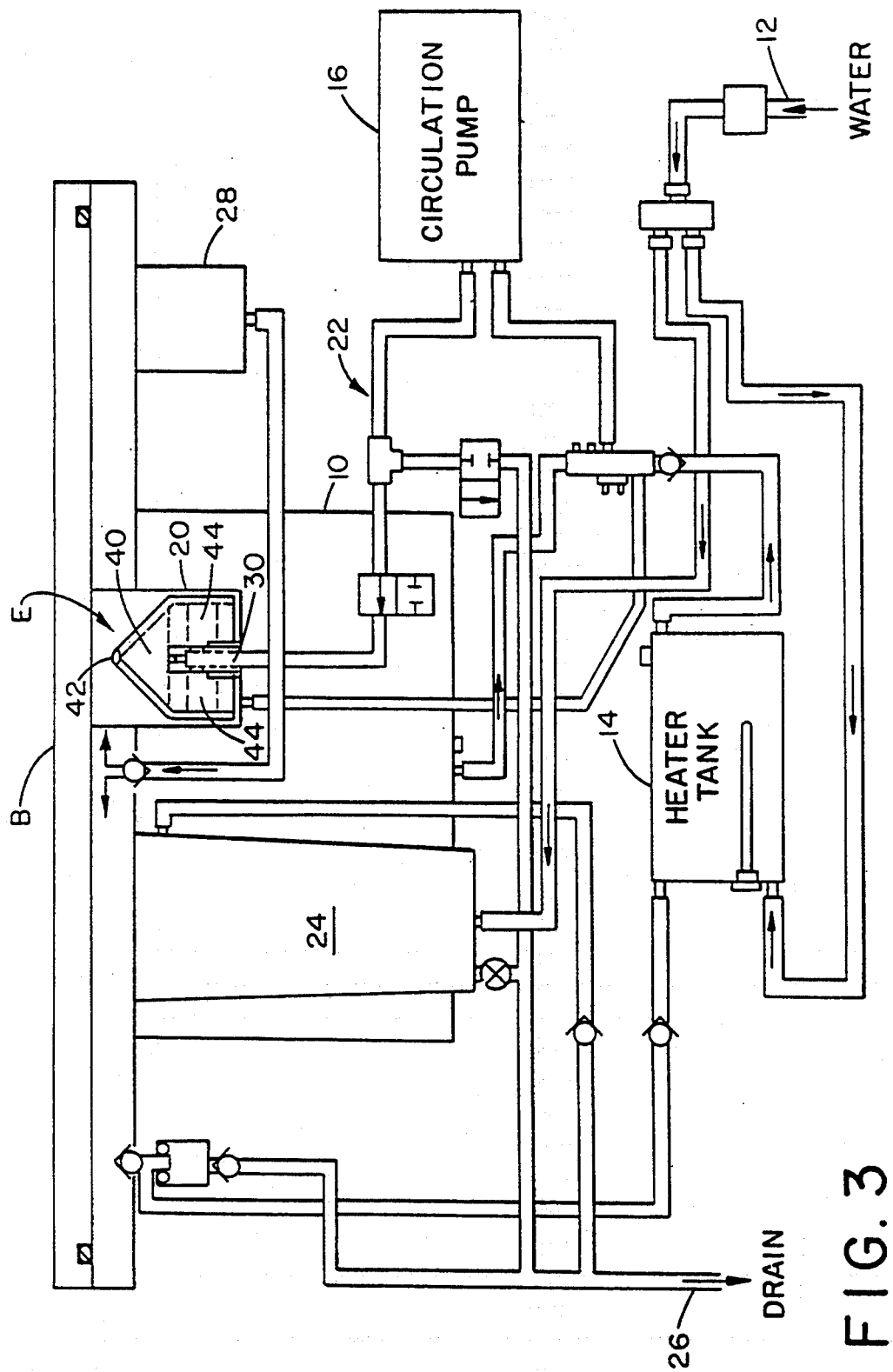
FIG. 3 is a plumbing diagram of the anti-microbial solution carrying paths of the decontamination unit of FIG. 1.

With particular reference to FIGS. 2 and 3, water from an inlet 12 is selectively heated in a heater tank 14 and circulated by a circulation pump 16 to a sterilant or other microbial decontamination solution mixing chamber 20. The mixing chamber 20 receives the cup D containing a premeasured dose of a microbial decontamination concentrate, preferably in powdered form. The water is sprayed into the cup or ampule D through the cutter assembly E, as discussed below, to for a sterilant or other anti-microbial solution.

After the circulation pump 16 circulates the heated water through the mixing chamber 20, the anti-microbial solution flows through a series of passageways 22 defined in part by the outer face of the housing A and the inner face of the door B. The passageways carry the anti-microbial solution over an inner surface of a rinse fluid sterilizing filter 24 and into the sterilizing or decontamination chamber 10. The anti-microbial solution is circulated through the flow passages such that every surface from the rinse water filter 24 downstream through the passages 22 and the decontamination chamber 10 are microbially decontaminated, preferably sterilized. After a preselected duration, the solution exits the apparatus at a drain 26 and rinse water is introduced. The rinse water flows into the filter 24 which filters at least all harmful microbes from the incoming water, i.e. at least disinfects the rinse water. The circulation pump 16 circulates the microbially decontaminated rinse water through the paths 22, the decontamination chamber 10, and the cassette or cartridge C. In order to prevent contamination from airborne microbes, an air microbe decontamination filter 28 filters air which is drawn into the system to replace the drained rinse and anti-microbial solutions.

Figure 4:
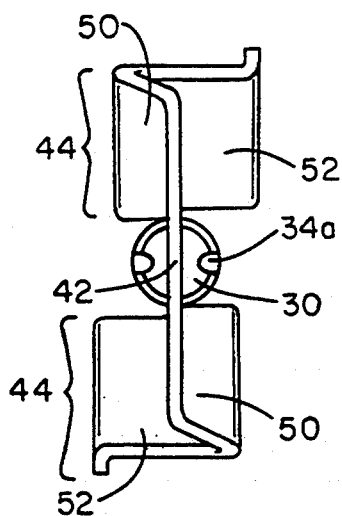
FIG. 4 is a top view of the cutter assembly of FIGS. 2 AND 3.
Figure 5:
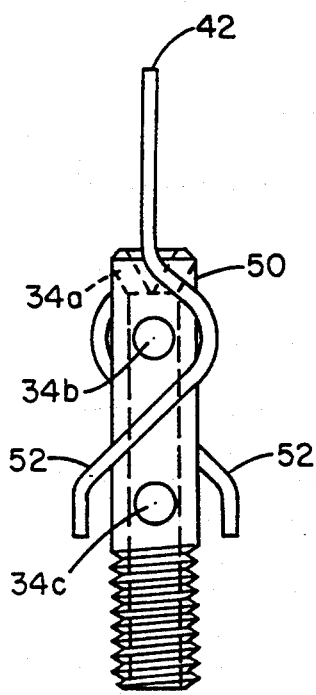
FIG. 5 is a side view of the cutter assembly.
Figure 6:
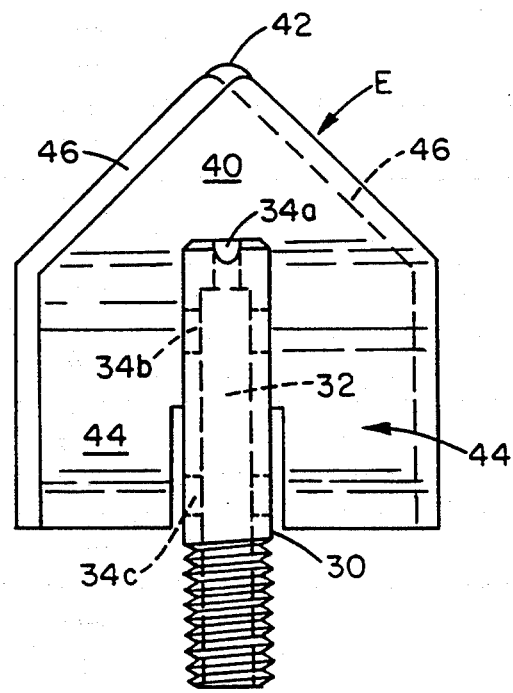
FIG. 6 is a front elevational view of the cutter assembly.

With continuing reference to FIGS. 2 and 3, and particular reference to FIGS. 4, 5 and 6, the anti-microbial mixing chamber 20 holds the cutter assembly E for selectively opening the reagent-containing cup D as it is inserted into the anti-microbial mixing chamber 20 and the door B is closed for use or sterilization to begin. The cutting assembly E includes a hollow central shaft 30 extending upward along the central axis of the well of mixing chamber 20. The shaft defines a hollow interior passage 32 in fluid communication with the circulation pump 16. Located along the axis of the shaft 30 are two upper apertures 34a that direct jets of water upward into an interior of the cup D. A pair of middle apertures 34b are positioned on opposite sides of the shaft 30 to direct jets of water transversely. A lower pair of apertures 34c directs water radially outward into the cup. Of course, the number of apertures 34 and the placement thereof on the shaft can be varied to suit larger or smaller units. Further, the apertures can be defined by round holes, slits, or other appropriate configurations.

The apertures 34a, 34b and 34c communicate between the hollow passage 32 inside of the shaft 30 and the inside of the reagent cup D. The fluid under pressure that is discharged through these apertures, flushes and dissolves powdered reagents held in cup D. It will be understood by the skilled artisan that, depending on the size and power of the cups and the unit, a larger or smaller number of apertures may be provided.

Now then, affixed to the shaft 30 is a cutting blade or means 40, which rests or is seated across the horizontal, flat top surface of the shaft 30. The blade 40 has an apex portion 42 which extends above the shaft 30. The apex portion 42 pierces the bottom dome of the reagent cup D upon insertion of the cup into the chamber 20. The blade 40 has two like side sections 44 disposed on either side of the shaft extending downward below the apex portion 42. Cutting edges 46 slope in opposite directions away from apex portion downward along the side blade sections 44 terminating adjacent a bottom of the chamber 20. The cutting edges 46 are bevelled facing in opposite directions to aid in piercing and cutting the reagent cup D. The beveled cutting edges 42 each angle toward the front face of a corresponding blade side section and extend the full length of the blade, from the apex to the bottom thereof.

The blade 40 has curvilinear configuration which defines an upper cam surface 50 and an opposite facing lower cam surface 52. The upper cam surface 50 projects outward in the same direction as the bevelled face of the cutting edge. The cam surface engages a cut edge of the cup just after it has been cut by the cutting edge 46. The lower cam surface 52 projects opposite to the upper cam surface. The lower cam surface engages an opposite cut edge of the cup. Together the upper and lower cam surfaces hold the cut portions of the cup open.

The curvilinear blade configuration sweeps around the middle apertures 34b and the lower apertures 34c.

The under surfaces of the cams deflect jets of water from the apertures and swirling water in the chamber 20 to enhance water flow and a complete flushing of all reagents from the cup.

Figure 7:
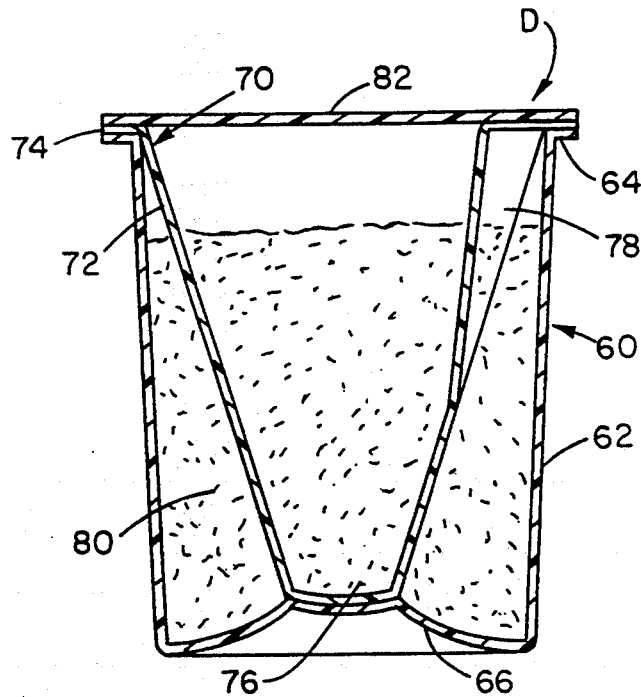
FIG. 7 is a sectional view of a reagent cup or package.

With reference to FIG. 7, the reagent cup D includes a first or outer cup 60 that holds a first powdered reagent. The outer cup 60 includes a cylindrical peripheral wall 62 that has a flange 64 at a first, open end thereof. A domed base wall 66 closes a second, opposite end of the peripheral wall. The outer cup is constructed of a light weight polymeric material, such as a styrene plastic, which has sufficient resiliency that the domed base wall 66 functions as a spring.

A second or inner cup portion 70 is received in the first cup portion 60. The second cup portion has a generally conical peripheral wall 72 that has a flange 74 integrally molded at a first, open end thereof. A base wall 76 closes a second end of the peripheral wall. The inner cup holds a first powdered reagent.

The first and second cup portions are configured such that when the flanges 64, 74 are abutting and sealed together, the base walls 66, 76 abut and flex the dome 66 slightly.

The second peripheral wall 72 has a recessed groove 78 that extends longitudinally there along to define access for filling an annular outer compartment 80 defined between the inner cup peripheral wall 72 and the outer cup peripheral wall 62 with a second powdered reagent. When the cutter assembly E enters the cup from the bottom, there is a tendency for one or both of the cups to collapse under the force of the cutter blade rather than being cut. The conical inner cup peripheral wall 72 interacts with the outer cup peripheral wall 62 to provide increased structural rigidity against vertical compression. A closure 82 is adhered to the flange 74 to seal the two chambers concurrently.

In use, as the reagent cup D is pressed down onto the cutting blade 40, the base wall 62 engages the blade apex portion 42. Further pressure causes the cutting edges 46 to slice from the puncture point through the bottom wall 62 and the inner and outer peripheral walls 62, 72. With continued pressure, the blade side portion 44 cuts through the inner and outer cup peripheral walls 52, 62. The cam surfaces 50, 52 of the blade 40 cam the edges of the cup peripheral walls open extending the cut higher.

After the door B is closed and a decontamination cycle is started, the hot water is pumped into the shaft 30. The water sprays through the upper jets or apertures 34a and sprays into the upper reaches of the inner cup. Water spraying through the center and lower jets or apertures 34b and 34c spray into the central and lower regions of both compartments. The serpentine configuration of the blades 40 serves to deflect fluid spray to further ensure total removal of all reagent matters from both chambers of the cup D.

Various anti-microbial agents may be utilized. In the preferred embodiment, the anti-microbial agent is a mixture of powders which reacts when wet to form a sterilant, such as a strong oxidant, corrosion inhibitors, and a wetting agent. More specific to the preferred embodiment, the dry ingredients include a water-soluble acid precursor and a water-soluble persalt which, when dissolved in water, form a peracetic acid solution with an anti-microbially effective concentration of peracetic acid. The dry ingredients further include a buffer, e.g. a borate, for bringing the pH to a neutral level to inhibit steel corrosion. The dry ingredients include other corrosion inhibitors, such as a molybdate for inhibiting steel corrosion, a triazole for inhibiting copper and brass corrosion, and the like. Powdered wetting and sequestering agents may also be included. In the preferred embodiment, the acid precursor is acetylsalicylic acid and the persalt is sodium perborate. The total volume of dry ingredients is such that the resultant water solution has a concentration of peracetic acid of at least 0.2% W/V of a biocidally effective concentration.

Other oxidizing or anti-microbial agents can also be generated in situ, such a chlorine dioxide, chlorine, hydrogen peroxide, and mixtures thereof. For example, the powdered ingredients may include a mixture of potassium chromates, sodium chloride, and phosphates. As another example, hydrogen peroxide can be generated from a mixture of sodium borate and phosphates. Chlorine dioxide can be generated from a mixture of sodium chlorate and lithium chlorite. Sodium chloride can be added to peracetic acid to produce hyperchlorous acid.

Other copper and brass corrosion inhibitors are also contemplated, such as benzotriazoles, polytriazoles, mercaptobenzathiozol, azoles, benzoates, and other five-membered ring compounds. Other anti-corrosives include chromates, dichromates, tungstates, vanidates, borates, and combinations thereof. A suitable sequestering agent for sequestering any precipitated calcium and magnesium salts is sodium hexametaphosphate.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A decontamination system comprising:
   a body portion including a water receiving inlet, a drain outlet, a decontamination region for receiving items to be decontaminated, and a well which receives a reagent cup;
   a means for defining fluid flow paths among the inlet, the reagent cup receiving well, the decontamination region, and a rinse fluid source;
   a fluid circulating means for selectively circulating fluid through the fluid flow paths and among the inlet, the heating means, the rinse fluid source, the decontamination region, and the reagent cup receiving well;
   a cutting blade assembly disposed in the reagent cup receiving well, the cutting assembly comprising:
      a central shaft extending vertically upward from the base of the well, the shaft defining a hollow interior passage and receiving fluid flow from the fluid circulating system, the shaft further having at least two apertures communicating between the hollow interior passage and the outside of the shaft for directing fluid flow into a received reagent cup;
      a cutting blade mounted on the central shaft and having an apex for puncturing a bottom of the received reagent cup, the cutting blade being divided by the central shaft to form two opposite blade sections on opposing sides of the central shaft;

each blade section having a cutting edge for cutting the received reagent cup and a curvilinear configuration for camming opening the reagent cup and deflecting fluid flow into the cup to promote complete flushing of reagents from the received reagent cup.

2. The system as set forth in claim 1 wherein the central shaft upper has apertures at the top which define upward directed jets and lower apertures on the lower portion thereof.

3. The system as set forth in claim 2 wherein the lower apertures are positioned on opposing sides of the central shaft and directed parallel to the blade sections.

4. The system as set forth in claim 1 wherein the cutting edges of the respective blade sections are bevelled with bevels that face in opposite directions.

5. The system as set forth in claim 1, wherein the curvilinear configuration of each blade section defines an upper cam surface that projects to one side of the central shaft and a lower cam surface that projects to an opposite side of the central shaft whereby the cam surfaces engage and separate cut edges of the reagent cup.

6. The system as set forth in claim 5 wherein fluid directed from a lower pair of apertures is deflected by the curved blade sections into the reagent cup to promote complete flushing of the reagents from the cup.

7. The system as set forth in claim 1 wherein the received reagent cup includes:
   a first cup portion having an outer peripheral wall and a base wall;
   a second cup portion having a base wall which is smaller in diameter and abuts the base wall of the first cup portion and an inner peripheral wall which extends upward from the second base wall such that an inner reagent chamber and an annular outer reagent chamber are defined;
   a closure spanning the outer peripheral wall to close the inner and outer reagent chambers.

8. The system as set forth in claim 7 wherein the inner peripheral wall tapers radially outward and abuts the outer peripheral wall at a top edge thereof such that the inner peripheral wall reinforces the base wall to inhibit the reagent cup from collapsing during cutting.

9. The system as set forth in claim 7 wherein the reagents include a first powdered component in the inner chamber and a second component in the outer chamber the first and second powdered components reacting in the fluid to form an oxidant.

10. A cutting blade assembly for cutting open a reagent containing package, the cutting blade assembly comprising:
    a central shaft extending vertically upward from a base, the shaft defining a hollow interior passage and being capable of receiving fluid flow from a fluid circulating system, the shaft further having at least two apertures communicating between the hollow interior passage of the shaft and the outside of the shaft for directing fluid flow into the reagent containing package;
    a cutting blade mounted on the central shaft and having an apex for puncturing a bottom of the reagent package, the cutting blade being divided by the central shaft to form two opposite but similar blade sections on opposing sides of the central shaft;
    each blade section having a cutting edge and a curvilinear configuration deflecting fluid flow into the reagent containing package to promote complete mixing of the reagent and fluid.

11. The blade assembly as set forth in claim 10 wherein the curvilinear configuration of each blade section defines an upper cam surface that projects to one side of the central shaft and a lower cam surface that projects to an opposite side of the central shaft whereby the cam surfaces engage and separate cut edges of the reagent package.

12. The blade assembly as set forth in claim 11 wherein the central shaft has:
    upper apertures on opposing sides of the cutting blade apex;
    central apertures in a central portion of the central shaft adjacent the upper cam surface such that fluid directed therefrom is deflected into the reagent package; and
    lower apertures in a lower portion of the centered shaft adjacent the lower cam surface such that fluid directed therefrom is deflected into the reagent package.

13. A combination frangible, two compartment cup and cutting blade assembly comprising:
    an outer peripheral cup wall;
    a base wall closing a lower end of the outer peripheral wall;
    an inner peripheral wall extending upward from the base wall and displaced radially inward from the outer peripheral wall such that an inner compartment is defined within the inner peripheral wall and an annular compartment is defined between inner and outer peripheral walls;
    a central shaft extending vertically upward from the base a reagent cup receiving well, the shaft having a hollow inside passage and carrying a fluid flow from a fluid circulating system, the shaft defining at least two apertures communicating between the hollow inside passage and the outside of the shaft for directing jets of fluid into the reagent cup;
    a cutting blade mounted on the central shaft and having an apex for puncturing the base wall, the cutting blade being divided by the central shaft to form two opposite blade sections on opposing sides of the central shaft;
    each blade section having a cutting edge for cutting through the inner and outer peripheral walls defining cut edges thereby and a curvilinear configuration for camming opening the cut edges of the peripheral walls.

14. The combination two compartment cup and cutting blade assembly as set forth in claim 13 wherein the curvilinear configuration of each blade section defines an upper cam surface that projects to one side of the central shaft and a lower cam surface that projects to an opposite side of the central shaft whereby the cam surfaces engage and separate cut edges of the reagent cup.

15. The combination two compartment cup and cutting blade assembly as set forth in claim 13 wherein the central shaft has upper apertures on opposing sides of the cutting blade apex and lower apertures on a lower portion of the central shaft for directing jets of fluid generally parallel to the blade sections such that fluid released therefrom is deflected by the curvilinear blade configuration into the reagent cup inner and outer compartments.

16. A method of opening a frangible package comprising:

inserting a package, which has a base wall and a peripheral wall, base wall first into a package receiving well;

as the package is received, piercing the base wall at the center thereof with an apex portion of a cutting blade;

with continued insertion of the package into the well, cutting deeper into the base wall and cutting into the peripheral walls with downward sloping edges of the cutting blade;

with continued insertion of the package into the well, camming apart portions of the base and peripheral walls adjacent the cuts made by the cutting blade.

17. The method as set forth in claim 16 wherein the package contains a dry reagent in an interior thereof and further including flushing the reagent with jets of water directed into the interior of the package.

18. The method as set forth in claim 17 wherein the package has concentric inner and outer peripheral walls that define an inner compartment and an outer annular compartment, one of the compartments containing a powdered acid precursor and the other containing a powdered persalt and further including:

reacting the acid precursor and the persalt in situ in the water to form a oxidant solution.

* * * * *